US012672973B2

(12) United States Patent
Sakurada

(10) Patent No.: US 12,672,973 B2
(45) Date of Patent: Jul. 7, 2026

(54) DELIVERY DEVICE AND METHOD FOR INDWELLING STENT

(71) Applicant: OLYMPUS MEDICAL SYSTEMS CORP., Tokyo (JP)

(72) Inventor: Yoichi Sakurada, Tachikawa (JP)

(73) Assignee: Olympus Medical Systems Corp., Tokyo (JP)

( * ) Notice: Subject to any disclaimer, the term of this patent is extended or adjusted under 35 U.S.C. 154(b) by 786 days.

(21) Appl. No.: 17/979,089

(22) Filed: Nov. 2, 2022

(65) Prior Publication Data

US 2023/0140867 A1     May 11, 2023

Related U.S. Application Data

(60) Provisional application No. 63/275,989, filed on Nov. 5, 2021.

(51) Int. Cl.
*A61F 2/966*     (2013.01)
*A61F 2/95*     (2013.01)

(52) U.S. Cl.
CPC ............ *A61F 2/966* (2013.01); *A61F 2/9517* (2020.05); *A61F 2/95* (2013.01)

(58) Field of Classification Search
CPC .. A61F 2/95; A61F 2/962; A61F 2/966; A61F 2/9517; A61F 2250/0065; A61B 2017/00243
See application file for complete search history.

(56) References Cited

U.S. PATENT DOCUMENTS

| | | | |
|---|---|---|---|
| 5,534,007 A | | 7/1996 | St. Germain et al. |
| 6,146,415 A | * | 11/2000 | Fitz ........................... A61F 2/95 |
| | | | 606/171 |
| 6,302,893 B1 | | 10/2001 | Limon et al. |
| 8,641,752 B1 | * | 2/2014 | Holm ..................... A61F 2/966 |
| | | | 623/1.12 |
| 9,125,761 B2 | * | 9/2015 | Wood ........................ A61F 2/95 |
| 9,414,915 B2 | * | 8/2016 | Lombardi ............. A61F 2/2418 |

OTHER PUBLICATIONS

Office Action dated Jan. 27, 2026, issued in corresponding Chinese Patent Application No. 202211363290.7.

* cited by examiner

*Primary Examiner* — Dinah Baria
(74) *Attorney, Agent, or Firm* — Morgan, Lewis & Bockius LLP

(57) ABSTRACT

A delivery device includes a handle, a first sheath having a proximal end portion connected to the handle, a second sheath through which the first sheath is inserted, the second sheath translatable relative to the handle in a longitudinal direction of the delivery device, a third sheath through which the second sheath is inserted and a length adjustment mechanism. A distance in the longitudinal direction of the delivery device between a proximal end of the first sheath and a distal end of the third sheath defines a separation distance. The length adjustment mechanism adjusts the separation distance between a first length and a second length. The second length is longer than the first length.

8 Claims, 10 Drawing Sheets

DELIVERY DEVICE AND METHOD FOR INDWELLING STENT

RELATED APPLICATION DATA

This application is based on and claims priority under 35 U.S.C. § 119 to U.S. Provisional Application Nos. 63/275, 989 was filed on Nov. 5, 2021. The entire contents of each of these applications are incorporated herein by reference.

FIELD OF THE DISCLOSURE

The present disclosure relates to a delivery device and a method for indwelling a stent.

BACKGROUND

A stent delivery device is used when a self-expanding stent is indwelled inside a body cavity (for example, specification of U.S. Pat. No. 6,302,893). In stent delivery devices in the related art, a stent is accommodated in a gap between an inner sheath and an outer sheath. The stent is exposed and increased in diameter by retracting the outer sheath with respect to the inner sheath. Thereafter, the stent is indwelled inside a body cavity by withdrawing the inner sheath from the stent.

SUMMARY

A delivery device includes a handle, a first sheath having a proximal end portion connected to the handle, a second sheath through which the first sheath is inserted, the second sheath translatable relative to the handle in a longitudinal direction of the delivery device, a third sheath through which the second sheath is inserted and a length adjustment mechanism. A distance in the longitudinal direction of the delivery device between a proximal end of the first sheath and a distal end of the third sheath defines a separation distance. The length adjustment mechanism adjusts the separation distance between a first length and a second length. The second length is longer than the first length.

A delivery device includes a first sheath, a second sheath through which the first sheath is inserted, the second sheath translatable relative to the handle in a longitudinal direction of the delivery device. The delivery device includes a third sheath having a channel extending therein. The second sheath is inserted through the channel and the second sheath is translatable in the channel relative to the third sheath in the longitudinal direction of the delivery device. The delivery device includes a length adjustment mechanism. The length adjustment mechanism adjusts a length of the second sheath inserted through the channel between a first length and a second length. The second length is longer than the first length.

A method for indwelling a stent includes steps of inserting a sheath main body of a delivery device into a channel of an endoscope. The sheath main body of the delivery device includes a first sheath, a second sheath through which the first sheath is inserted, the second sheath translatable relative to the handle in a longitudinal direction of the delivery device, and a third sheath having a sheath channel extending therein. The second sheath is inserted through the sheath channel and the second sheath is translatable in the sheath channel relative to the third sheath in the longitudinal direction of the delivery device. The method for indwelling a stent includes steps of fixing a position of the sheath main body in the longitudinal direction of the delivery device relative to the channel of the endoscope. The method for indwelling a stent includes steps of retracting the second sheath to cause a part of a stent accommodated in a distal end portion of the sheath main body to protrude from the delivery device. The method for indwelling a stent includes steps of changing a length of the second sheath inserted through the sheath channel between a first length and a second length by advancing the second sheath relative to the third sheath, where the second length is longer than the first length. Advancing the second sheath causes the stent to be accommodated inside the sheath main body.

BRIEF DESCRIPTION OF DRAWINGS

FIG. 2 is a cross-sectional view of a delivery device according to the first embodiment.

FIG. 11 is a cross-sectional view of a delivery device according to a third embodiment.

DETAILED DESCRIPTION

First Embodiment

Figure 1:
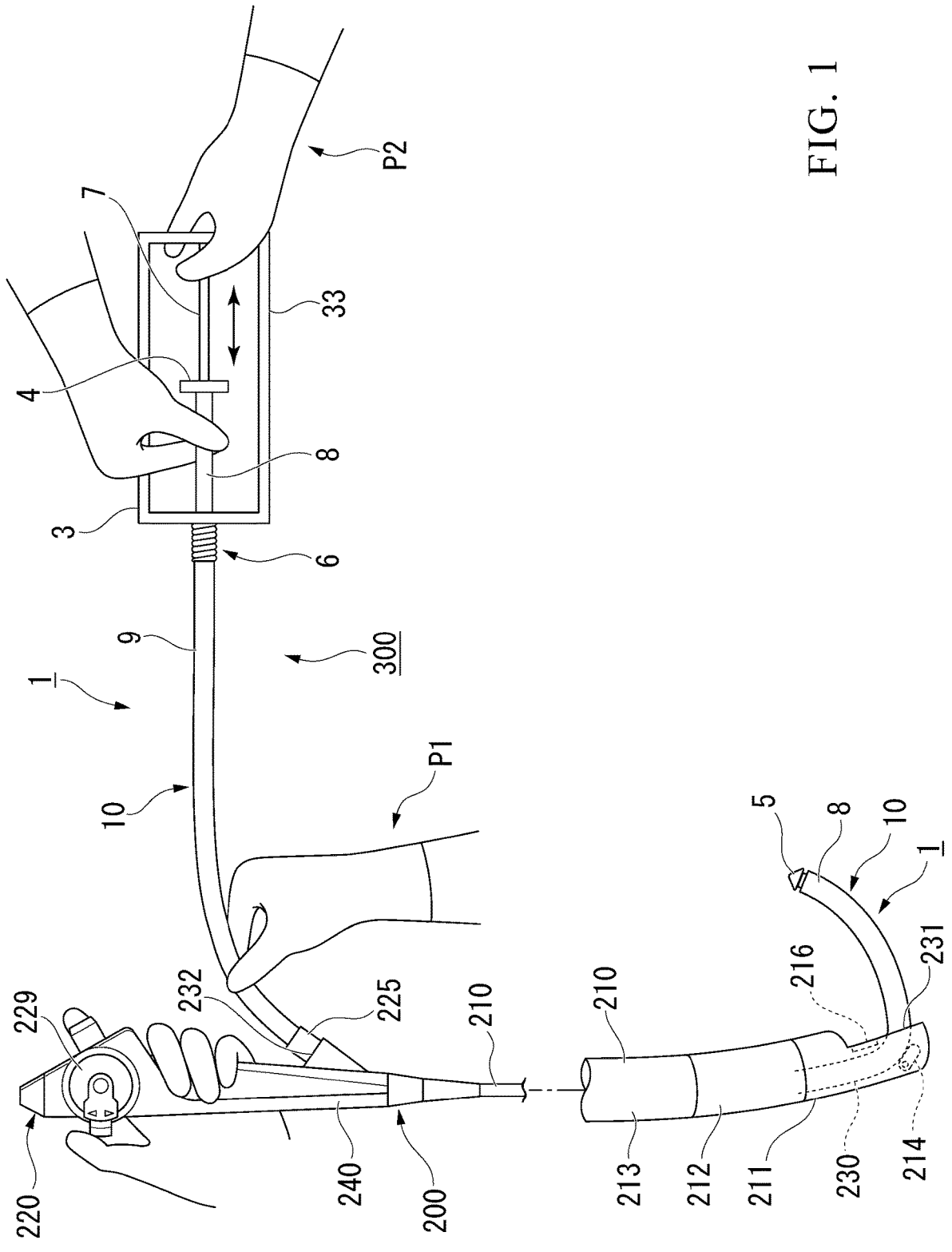
FIG. 1 is an overall view of a delivery system according to a first embodiment.

A delivery system 300 according to a first embodiment will be described with reference to FIGS. 1 to 3. FIG. 1 is an overall view of the delivery system 300 according to the present embodiment.

[Stent Delivery System 300]

As illustrated in FIG. 1, the stent delivery system 300 includes an endoscope 200 and a delivery device 1. The delivery device 1 is used by being inserted into the endoscope 200. FIG. 1 illustrates a distal portion of the delivery device 1 in an enlarged manner.

[Endoscope 200]

The endoscope 200 is a known side view-type flexible endoscope. The endoscope 200 is provided with an elongated insertion portion 210, an operation portion 220, a treatment tool channel 230 (which will hereinafter be referred to as "a channel 230"), and a gripped portion 240. The operation portion 220 is provided in a proximal end portion of the insertion portion 210. In the following description, the operation portion 220 side of the endoscope 200 will be referred to as a proximal side L2. A side of the insertion portion 210 opposite to the operation portion 220 in a longitudinal direction will be referred to as a distal side of the endoscope 200. The channel 230 is inserted through a treatment tool such as the delivery device 1. The endoscope 200 may be a direct view-type flexible endoscope.

The insertion portion 210 has a distal end hard portion 211, a bending portion 212, and a flexible tube portion 213. The distal end hard portion 211 is provided in a distal end portion of the insertion portion 210. The bending portion 212 is attached to a proximal side of the distal end hard portion 211 and configured to perform bending operation. The flexible tube portion 213 is attached to the proximal side L2 of the bending portion 212.

An imaging unit 216 is provided on a side surface of the distal end hard portion 211 in a state of being exposed to the outside. The imaging unit 216 has a light guide and a CCD.

A raising base 214 is provided in the distal end hard portion 211. A proximal end portion of the raising base 214 is rotatably supported by the distal end hard portion 211. A raising base operation wire (not illustrated) is fixed to a distal end portion of the raising base 214. The raising base operation wire (not illustrated) extends to the proximal side L2 through the inside of the insertion portion 210.

The bending portion 212 is configured to be freely bent in a vertical direction and a lateral direction. In the bending portion 212, a distal end of an operation wire is fixed to a distal side of the bending portion 212. The operation wire extends to the operation portion 220 through the inside of the insertion portion 210. In a direction intersecting the axis and bent in orthogonal directions from a state in which the insertion portion 210 extends straight, the vertical direction is a vertical direction of the field of view of the endoscope. In the direction intersecting the axis and bent in orthogonal directions from the state in which the insertion portion 210 extends straight, the lateral direction is a lateral direction of the field of view of the endoscope. A bending direction of the bending portion 212 is not limited to the vertical direction and the lateral direction, and a bending direction may be freely bent in a direction intersecting the axis of the insertion portion 210. The bending portion 212 is bent in accordance with an operation of the operation portion 220 by a surgeon.

A distal opening 231 of the channel 230 opens on the side surface of the distal end hard portion 211. A proximal end portion of the channel 230 extends to the gripped portion 240. The gripped portion 240 is gripped by a surgeon P1 of the endoscope 200. A forceps port 232 communicating with the channel 230 is provided in the gripped portion 240. The surgeon can insert an endoscopic treatment tool such as the delivery device 1 through the forceps port 232. A forceps plug 225 for preventing leakage of a body fluid is attached to the forceps port 232.

The operation portion 220 is connected to the insertion portion 210. The operation portion 220 has an input portion 229. The input portion 229 receives an operational input for bending motion of the bending portion 212, an operational input for the imaging unit 216, and the like. A universal cord (not illustrated) is connected to the operation portion 220. The universal cord is connected to a display device such as a liquid crystal display via an image processing device including a processor and the like. An image captured by an imaging portion 203 is output to the outside via the universal cord.

[Delivery Device 1]

Figure 2:
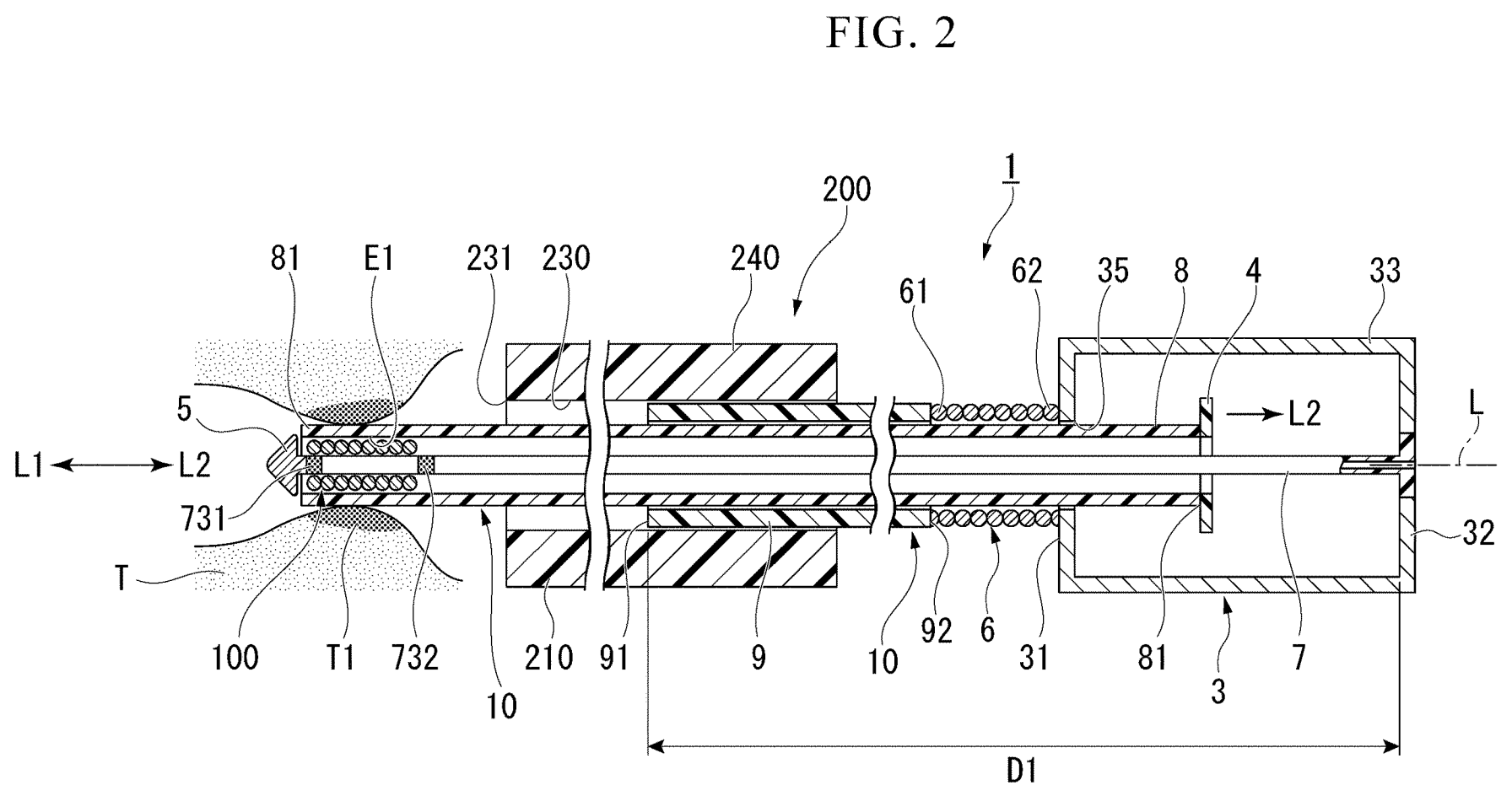
Figure 3:
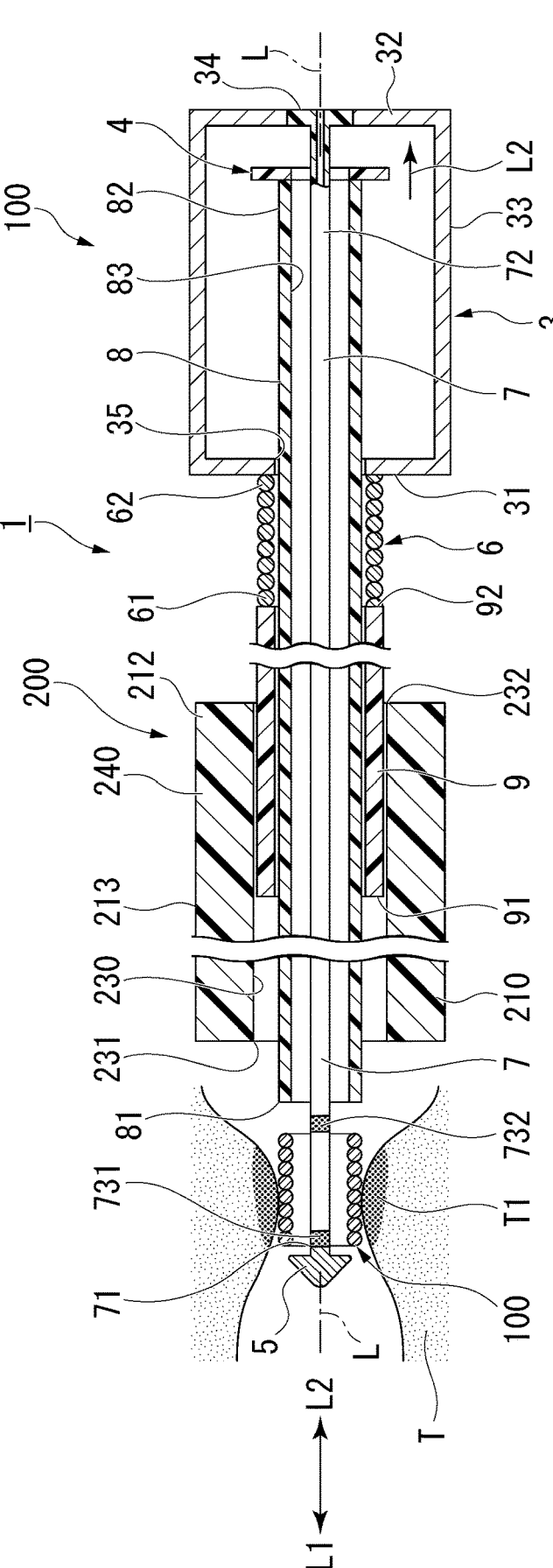
FIG. 3 is another cross-sectional view of the delivery device according to the first embodiment.

FIGS. 2 and 3 are cross-sectional views in a longitudinal direction L of the delivery device 1. The delivery device 1 has an elongated shape in its entirety. FIGS. 2 and 3 illustrate the delivery device with a part broken in the longitudinal direction. The delivery device 1 includes a first sheath 7, a second sheath 8, a third sheath 9, a handle 3, and an adjuster 6. The first sheath 7, the second sheath 8, and the third sheath 9 constitute a sheath main body 10. In the following description, in the longitudinal direction L of the delivery device 1, a side to be inserted into the body of a patient will be referred to as "a distal side L1", and the handle 3 side will be referred to as "a proximal side L2".

The sheath main body 10 has flexibility and extends from a distal end to a proximal end. The sheath main body 10 has the first sheath 7, the second sheath 8, and the third sheath 9 in order from the inward side. The first sheath 7, the second sheath 8, and the third sheath 9 are arranged in a substantially concentric state. Each of the first sheath 7, the second sheath 8, and the third sheath 9 is an elongated resin member. The first sheath 7 is inserted through a lumen 83 of the second sheath 8, and the second sheath 8 is inserted through the inside of a lumen 93 of the third sheath 9. The sheath main body 10 has an outer diameter so as to be inserted into the channel 230 of the endoscope 200 illustrated in FIG. 1. The sheath main body 10 is provided such that the channel 230 is capable of advancing and retracting. As illustrated in FIG. 1, in a state in which the sheath main body is inserted into the channel 230, distal ends of the first sheath 7 and the second sheath 8 are capable of protruding and retracting through the distal opening 231 of the channel 230.

A distal end 5 is attached to a distal end 71 of the first sheath 7. A diameter of the distal end 5 is larger than an inner diameter of the lumen 83 of the second sheath 8 and is equal to or smaller than an outer diameter of the second sheath 8. The distal end tip 5 abuts a distal end 81 of the second sheath 8 at a position where the first sheath 7 has retracted to the end. A proximal end 72 of the first sheath 7 is connected to the handle 3. Specifically, the proximal end 72 of the first sheath 7 is fixed to a fixing portion 34 of a proximal end portion 32 of the handle 3. A plurality of X-ray tips 731 and 732 are provided in a distal end portion of the first sheath 7 at positions away from each other in the longitudinal direction L. The X-ray tips 731 and 732 respectively indicate accommodation positions of a distal end and a proximal end of a stent 100 inside a body cavity at the time of indwelling of the stent.

The second sheath 8 has the distal end 81 on a distal side of the delivery device 1 and has a proximal end 82 on the proximal side L2 of the delivery device 1. As illustrated in FIGS. 2 and 3, the lumen 83 is formed in the second sheath 8 from the distal end 81 to the proximal end 82. The proximal end 82 of the first sheath 7 is fixed to an operation portion 4. The first sheath 7 is inserted through the inside of the lumen 83. The second sheath 8 may be a tube formed of a resin or the like or may be a coil sheath.

The second sheath 8 has a stent storage region E1 for storing the stent 100. The stent storage region E1 is a region for storing the stent 100, which has been inserted on the outward side of the first sheath 7, inside the lumen 83 of the second sheath 8. In the stent storage region E1, the stent 100 is stored between an inner surface of the lumen 83 of the second sheath 8 and the first sheath 7. The stent storage region E1 is a region extending from the distal end 81 of the second sheath 8 to the proximal side L2 by the length of the stent 100 or longer. The stent storage region E1 positioned on the distal side of a distal end 91 of the third sheath 9.

The third sheath 9 constitutes an outermost layer of the sheath main body 10. The second sheath 8 is inserted through the inside of the lumen 93 of the third sheath 9. A proximal end 92 of the third sheath 9 is fixed to the adjuster 6. The third sheath 9 is attached to the handle 3 via the adjuster 6. The length of the third sheath 9 is shorter than those of the first sheath 7 and the second sheath 8. The third sheath 9 may have a length allowing the distal end 91 of the third sheath 9 to be disposed on the distal side of the forceps port 232 when the delivery device 1 is inserted into the channel 230 of the endoscope 200. The length of the third sheath 9 may be a length allowing the distal end 91 of the third sheath 9 to be inserted into the forceps port 232 and to be disposed on the proximal side of a proximal end of the stent storage region E1 of the second sheath 8. The distal end 91 of the third sheath 9 is positioned in an intermediate portion between the first sheath 7 and the second sheath 8 in the longitudinal direction L. The third sheath 9 may be a tube formed of a resin or the like or may be a coil sheath.

The adjuster 6 is configured to change a distance D1 between the proximal end 72 of the first sheath 7 and the distal end 91 of the third sheath 9 in the longitudinal direction L between a first distance and a second distance. The distance D1 corresponds to a separation distance. In other words, the adjuster 6 is configured to change an insertion length of the second sheath 8 inserted through the inside of the lumen 93 (path) of the third sheath 9 between a first length and a second length longer than the first length. In other words, the adjuster 6 is configured to adjust the separation distance between a first length and a second length. The lumen 93 might be called as a channel or sheath channel. The insertion length of the second sheath 8 is a length of which the second sheath 8 has been inserted into the lumen 83 of the third sheath 9. The lumen 93 of the third sheath 9 is sufficiently larger than the outer diameter of the second sheath 8. Therefore, a central axis of the second sheath 8 inside the lumen 93 does not always coincide with a central axis of the lumen 93 of the third sheath 9, and the second sheath 8 slightly meanders inside the lumen 93. The insertion length of the second sheath 8 meandering inside the lumen 93 becomes longer than an overall length of the lumen 93 of the third sheath 9. The adjuster 6 is attached to the handle 3. The adjuster 6 is provided between the proximal end 92 of the third sheath 9 and the handle 3. For example, the adjuster 6 is a tubular biasing member. For example, the adjuster 6 is a spring having a spring force of 3 N or smaller. In the present embodiment, an example in which the adjuster 6 is a coil spring will be described. The adjuster 6, the tubular biasing member or the spring may be called as a length adjustment mechanism.

The handle 3 is a part gripped by a surgeon P2 of the delivery device 1. The handle 3 has a distal end portion 31, the proximal end portion 32, and an intermediate portion 33. The distal end portion 31 and the proximal end portion 32 have flat plate shapes substantially orthogonal to the longitudinal direction L and are disposed away from each other in a parallel manner. The intermediate portion 33 extends in the longitudinal direction L and connect the distal end portion 31 and the proximal end portion 32 to each other. The fixing portion 34 of the proximal end portion 32 of the first sheath 7 is provided in the proximal end portion 32. In the distal end portion 31, an opening portion 35 is formed on the distal side L1 of the fixing portion 34. The opening portion 35 is an opening which penetrates the distal end portion 31 in the longitudinal direction L and has a size allowing the second sheath 8 to advance and retract.

A proximal end portion of the first sheath 7 is inserted through the opening portion of the handle 3, and the proximal end 72 is fixed to the fixing portion 34. A proximal end portion of the second sheath 8 is inserted through the opening portion 35 of the handle 3 and is provided so as to be capable of advancing and retracting with respect to the handle 3. The operation portion 4 fixed to the proximal end 82 of the second sheath 8 is provided so as to be movable between the distal end portion 31 and the proximal end portion 32 of the handle 3 in the longitudinal direction L. A proximal end 62 of the adjuster 6 is fixed to the distal end portion 31 of the handle 3. The proximal end 62 of the third sheath 9 is attached to the handle 3 with the adjuster 6 therebetween. Therefore, when the operation portion 4 is advanced and retracted in the longitudinal direction L with respect to the handle 3, the second sheath 8 relatively advances and retracts with respect to the first sheath 7 and the third sheath 9. The distance D1 between the proximal end 72 of the first sheath 7 and the distal end 91 of the third sheath 9 in the longitudinal direction L changes due to extension and contraction of the adjuster 6 in the longitudinal direction L. Therefore, path lengths of the first sheath 7 and the second sheath 8 inside the lumen 93 of the third sheath 9 change due to extension and contraction of the adjuster 6 in the longitudinal direction L.

Figure 4:
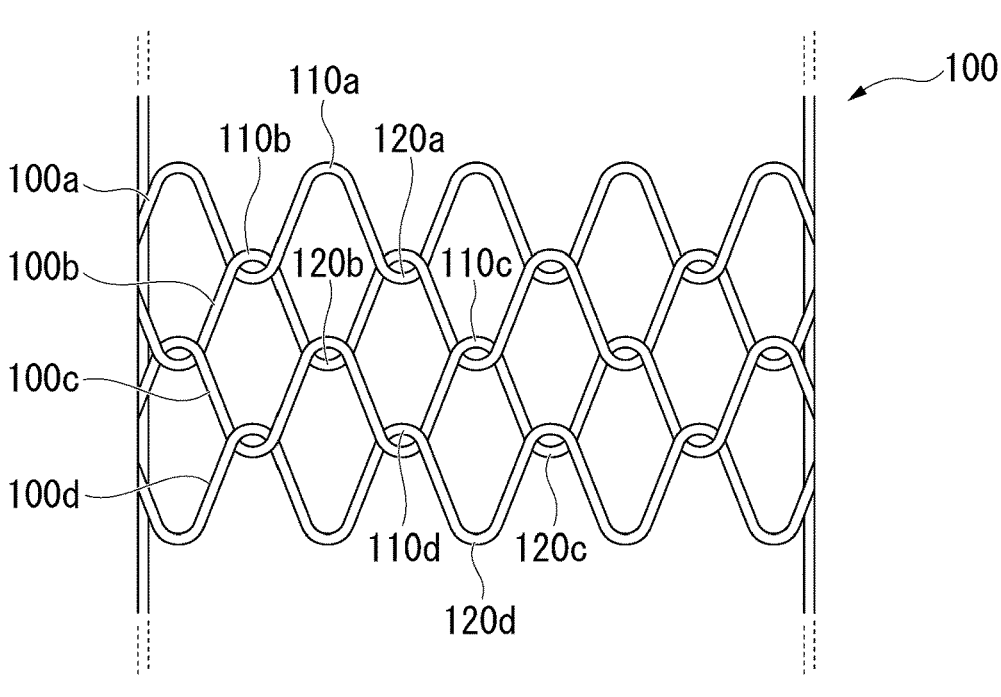
FIG. 4 is a side view of a stent.
Figure 5:
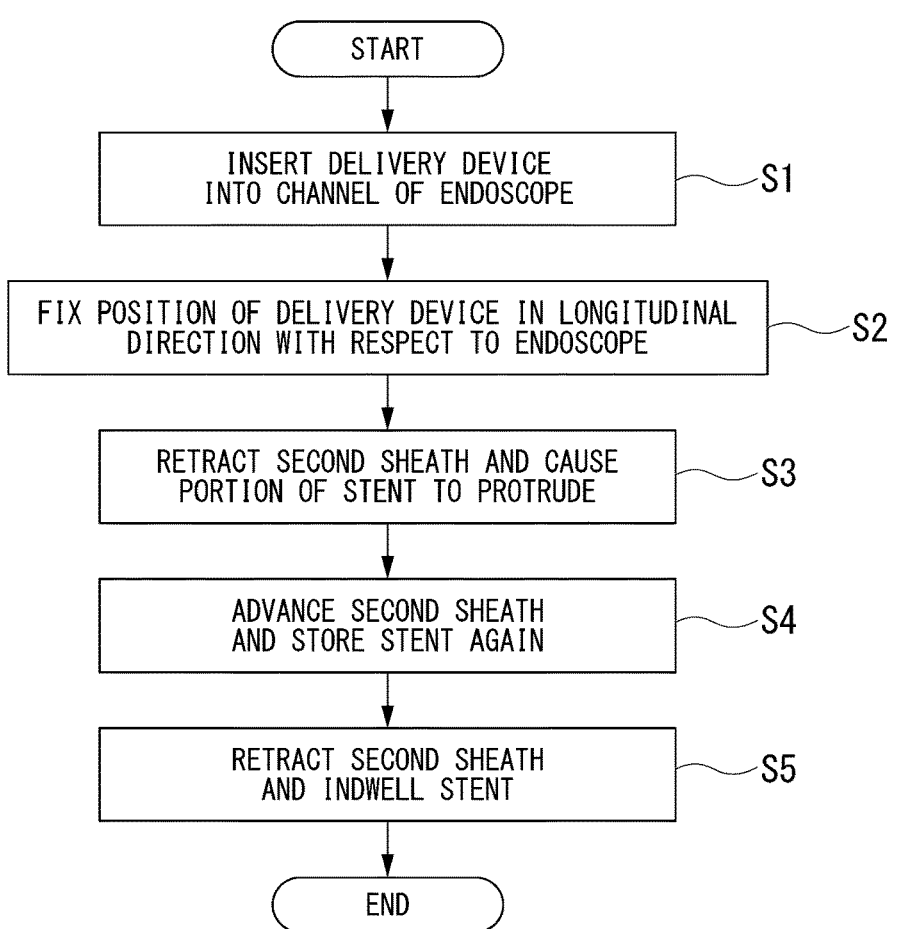
FIG. 5 is a flowchart of a stent delivery method according to the first embodiment.

The stent 100 is a tubular self-expanding stent. For example, the stent 100 is formed by weaving wires. For example, wires forming the stent 100 are made of a super-elastic alloy having NiTi as a main material. In a super-elastic alloy having NiTi as a main material, a woven shape is memorized in a woven state. FIG. 4 illustrates an example of a constitution of a main portion of the stent 100. As illustrated in FIG. 4, a plurality of ring-shaped wires 100*a*, 100*b*, and 100*c* are provided side by side in the longitudinal direction L. Each of the wires 100*a*, 100*b*, and 100*c* has first bent portions 110*a*, 110*b*, and 110*c* which are bent in a first direction of the longitudinal direction L and second bent portions 120*a*, 120*b*, and 120*c* which are bent in a second direction that is a direction different from the first direction. The second direction might be an opposite direction of the first direction. In each of the wires 100*a*, 100*b*, and 100*c*, a plurality of first bent portions 110*a*, 110*b*, and 110*c* and a plurality of second bent portions 120*a*, 120*b*, and 120*c* are alternately disposed in a circumferential direction. A plurality of wires 100*a*, 100*b*, and 100*c* form a tubular shape which extends in the longitudinal direction L and in which the plurality of first bent portions 110*a*, 110*b*, and 110*c* and the plurality of second bent portions 120*a*, 120*b*, and 120*c* intersect and knitted with each other. Intersecting parts of the plurality of first bent portions 110*a*, 110*b*, and 110*c* and the plurality of second bent portions 120*a*, 120*b*, and 120*c* will be referred to as engagement portions. The stent 100 can be further decreased in diameter than that in a natural state when an external force is applied thereto, and it has a strength capable of holding a lumen without blocking a stenosed site.

As illustrated in FIG. 2, the stent 100 is accommodated in the stent storage region E1 of the second sheath 8. Specifically, the first sheath 7 passes through the inside of the stent 100, and the stent 100 in a diameter-decreased state is accommodated in a gap between the first sheath 7 and the inner wall of the lumen 83 of the second sheath 8. The stent 100 is interlocked with an interlock portion (not illustrated) formed on an outer circumferential surface of the first sheath 7. Accordingly, the stent 100 is positionally set with respect to the first sheath 7 in a diameter-decreased state and does not relatively move in the longitudinal direction L of the first sheath 7. In the delivery device 1, the second sheath 8 moves to the proximal side L2 of the delivery device 1 and the stent 100 is released from a distal end of the delivery device 1 when the operation portion 4 is pulled to the proximal side L2 with respect to the handle 3. In addition, when the first sheath 7 is retracted in a state in which a portion of the stent 100 is accommodated within the stent storage region E1, the distal end tip 5 retracts while pushing the stent 100 to the proximal side L2, and the stent 100 can be accommodated within the stent storage region E1 again while decreasing in diameter.

Since the delivery device 1 is inserted through the inside of the insertion portion 210 of the endoscope 200 meandering inside a body cavity, the first sheath 7 and the second sheath 8 also meander. When the first sheath 7 and the second sheath 8 meander in this manner, a change occurs in the path length of the first sheath 7 inside the lumen 83 of the second sheath 8, and a protrusion length of the first sheath 7 protruding from the distal end 81 of the second sheath 8 changes. In the delivery device 1, when an active bending portion of the insertion portion 210 of the endoscope 200 is significantly bent in a state in which a portion of the sheath main body 10 protrudes through the distal opening 231 of the channel 230, the first sheath 7 and the second sheath 8 may be significantly bent. In this case as well, the protrusion length of the first sheath 7 also changes. Since the lumen 83 of the second sheath 8 is larger than an outer diameter of the first sheath 7, if the sheath main body 10 is significantly bent or meanders, the second sheath 8 is bent and meanders inside the lumen 83 of the second sheath 8, and the path length of the first sheath 7 inside the lumen 83 changes. In contrast, by providing the adjuster 6, the path length of the first sheath 7 inside the lumen 83 can be adjusted, and positional misalignment of the distal end tip 5 due to change in path length is prevented. That is, positional misalignment of an indwelling position of the stent 100 at the time of feeding operation of the stent 100 can be resolved.

[Method for Indwelling Stent]

Next, with reference to FIGS. 5 to 8, an example of a method for indwelling a stent and a method for using the delivery system 300 will be described. Specifically, a treatment in which the stent 100 is indwelled at a stenosed site T1 inside a body cavity using the delivery system 300 will be described as an example. A surgeon identifies an indwelling position of the stent 100 by a known method. For example, under X-ray illumination, while checking the position of the stenosed site T1 in a lumen, the insertion portion 210 of the endoscope 200 is inserted to a location in the vicinity of the stenosed site T1. The surgeon inserts the insertion portion 210 of the endoscope 200 into the digestive canal (for example, the esophagus, the stomach, the duodenum, or the large intestine) and identifies a stenosed site while observing images obtained by the imaging unit 216 of the endoscope 200.

Figure 6:
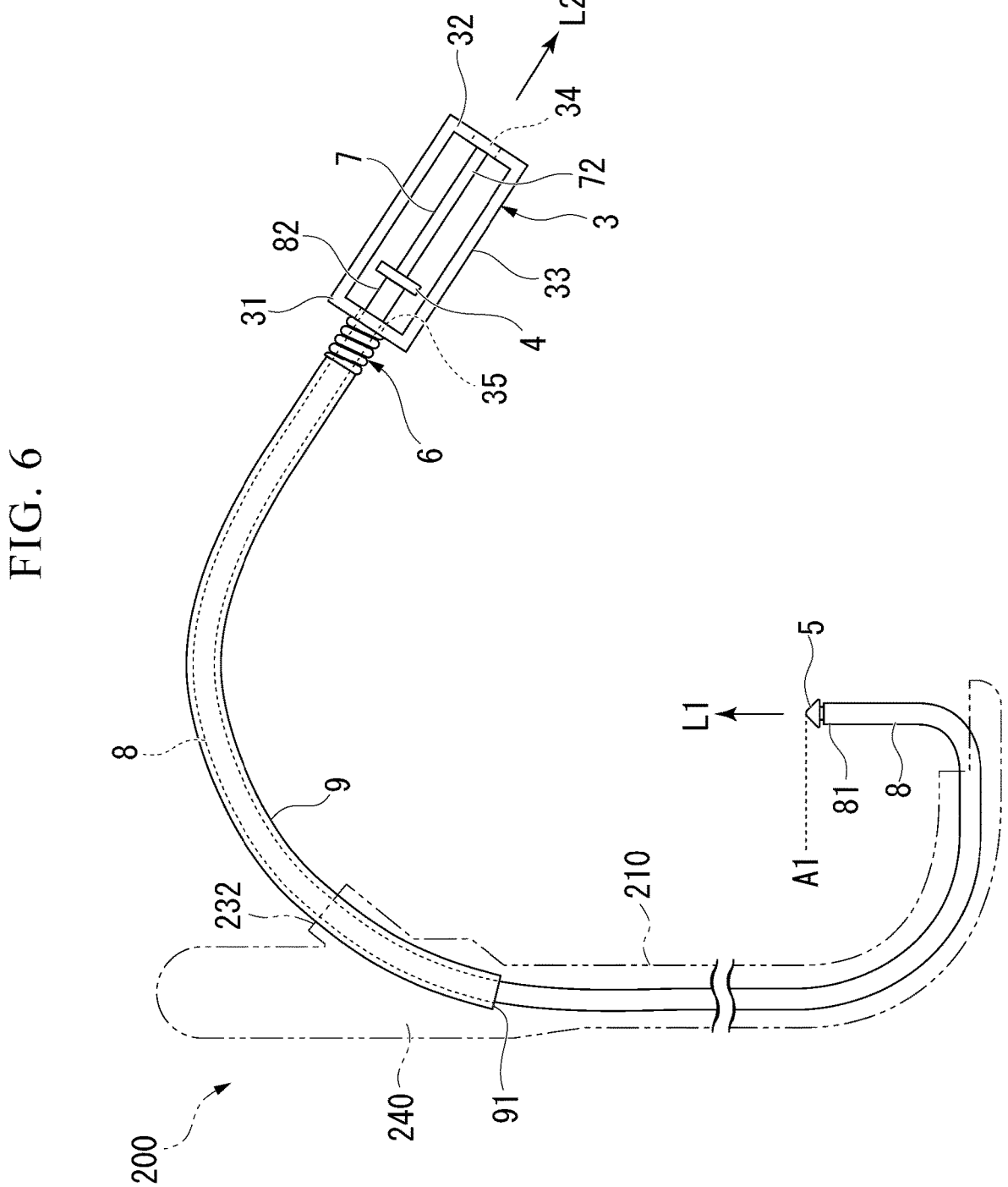
FIG. 6 is a view illustrating a step of the delivery method.

Next, the surgeon inserts the delivery device 1 into the channel 230 through the forceps port 232 and causes a distal end portion of the sheath main body 10 to protrude through the distal opening 231 of the insertion portion 210 as illustrated in FIG. 6 (Step S1). The delivery system 300 is operated by the surgeon P1 operating the endoscope 200 and the surgeon P2 operating the delivery device 1. When the surgeon P1 disposes the delivery device 1 in the vicinity of the stenosed site T1, the surgeon P1 grips the delivery device 1 in the vicinity of the forceps port 232 and fixes the position of the delivery device 1 in the longitudinal direction with respect to the insertion portion 210 (Step S2). At this time, the distal end 91 of the third sheath 9 is disposed on the distal side of the forceps port 232 inside the channel 230. In FIG. 6, as an example, the distal end 91 of the third sheath 9 is disposed at the position of the gripped portion 240 inside the channel 230. The surgeon P2 grips the handle 3 with one hand and grips the operation portion 4 with the other hand. The position of the distal end tip 5 with respect to the distal opening 231 of the insertion portion 210 of the endoscope 200 in Step S2 will be referred to as an advanced movement position A1.

Figure 7:
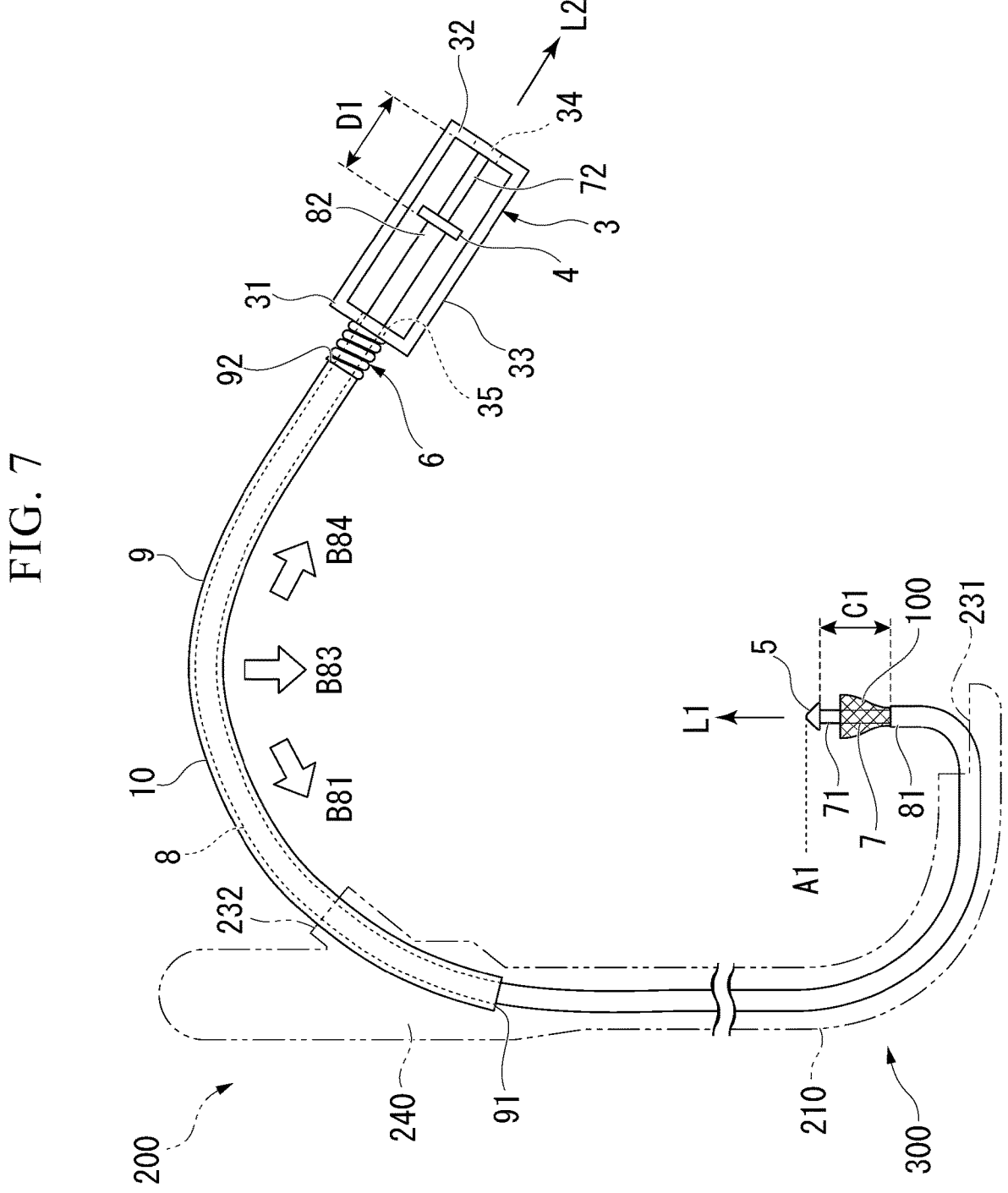
FIG. 7 is a view illustrating another step of the delivery method.
Figure 8:
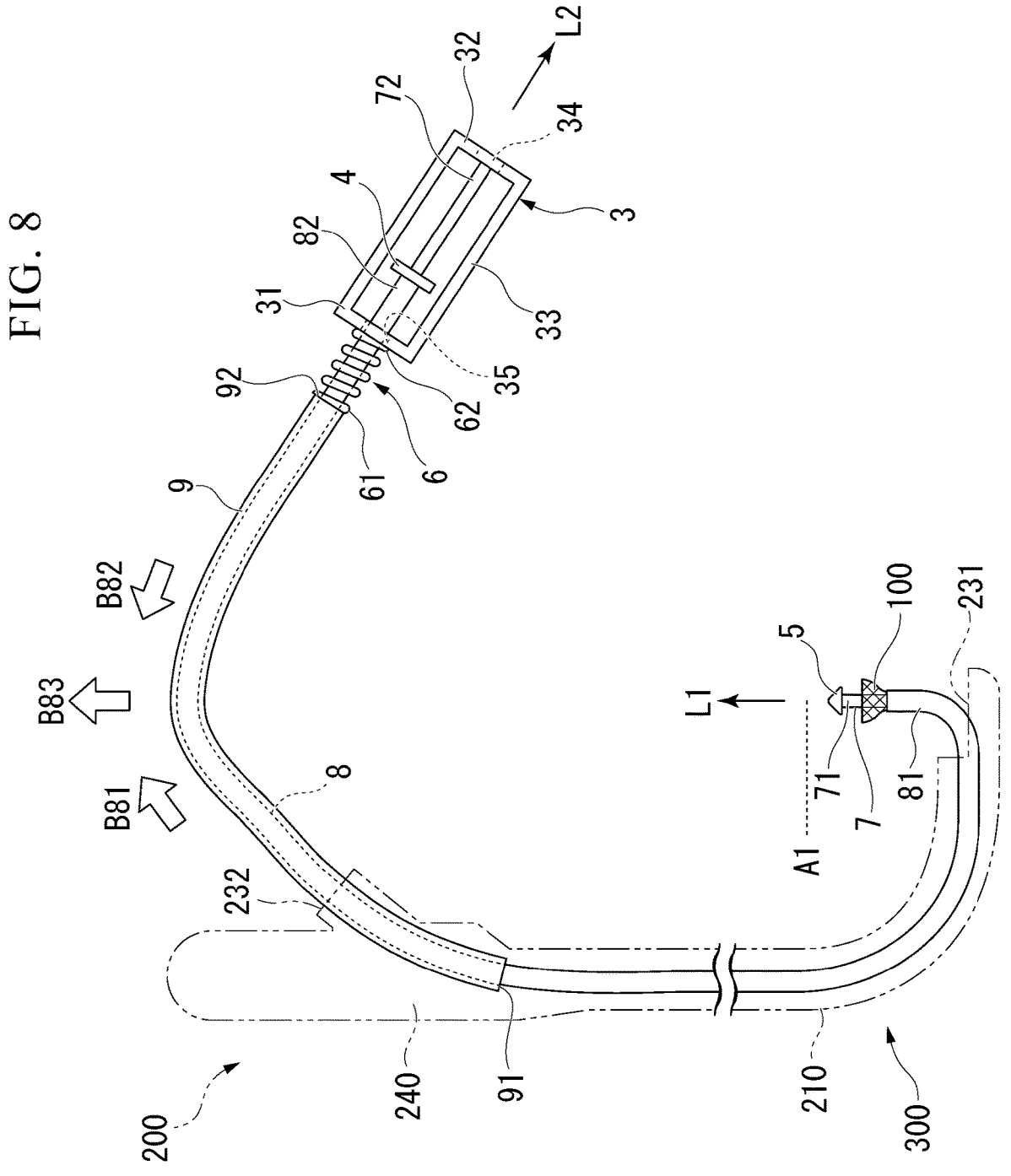
FIG. 8 is a view illustrating another step of the delivery method.

Next, as illustrated in FIG. 7, the surgeon P2 retracts the operation portion 4 to the proximal side L2 while holding the handle 3 and causes a portion of the stent 100 to protrude from the second sheath 8 (Step S3). In other words, in Step S3, the surgeon P2 retracts the second sheath to cause a part of a stent accommodated in a distal end portion of the sheath main body to protrude from the delivery device. Specifically, when the operation portion 4 is retracted with respect to the handle 3, the second sheath 8 retracts with respect to the first sheath 7. As a result, the distal end 71 of the first sheath 7 is in a state of protruding from the distal end 81 of the second sheath 8, and the distal portion of the stent 100 is exposed. Since a proximal end of the third sheath 9 is connected to the handle 3, if the position of the handle 3 is held, the position of the third sheath 9 with respect to the forceps port 232 and the channel 230 is held. For this reason, in the first sheath 7 connected to the third sheath 9 with the handle 3 therebetween, the distal end tip 5 is held at the advanced position A1 and a protrusion length thereof from the channel 230 is retained. At this time, static friction and kinetic friction of the stent 100 with respect to the outer circumferential surface of the first sheath 7 in the diameter-decreased part are sufficiently larger than kinetic friction of the stent 100 with respect to the inner wall of the lumen 83 of the second sheath 8. For this reason, a state in which the stent 100 is disposed in a distal end portion of the first sheath 7 is retained. The sheath main body 10 between the position in the delivery device 1 gripped by the surgeon P1 and the handle 3 can be freely bent in accordance with the position or the like of the handle 3. Relative positions of the first sheath 7, the second sheath 8, and the third sheath 9 in the sheath main body 10 at a time of being bent at which the sheath main body 10 is bent are different from that at a time of being straight at which the sheath main body 10 extends straight in the longitudinal axis direction. At the time of being straight, the lengths (path lengths) of the first sheath 7 and the second sheath 8 inside the third sheath 9 are substantially equivalent to each other. When the sheath main body 10 is significantly bent, the central axes of the first sheath 7 and the second sheath 8 inside the third sheath 9 are misaligned with each other, and the path lengths of the first sheath 7 and the second sheath 8 inside the third sheath 9 change. As illustrated in FIGS. 6 and 7, when the sheath main body is bent and the proximal end 82 of the second sheath 8 is pulled to the proximal side L2 in a state in which the positions of the first sheath 7 and the third sheath 9 are held, forces act on the second sheath 8 to the inward side of bending of the sheath main body 10, namely, in directions indicated by the arrows B81, B82, and B83 in FIG. 7. As a result, a force linearizing in the direction of the arrow B83 acts on the third sheath 9 from the second sheath 8 inside the lumen 93. However, in the state illustrated in FIG. 7, the adjuster 6 is in a compressed state and does not contract any further in the longitudinal direction L. For this reason, even if a linearizing force acts on the third sheath 9, it is not deformed in the direction of the arrow B83 due to a reaction force of the compressed adjuster 6, and thus linearization of the third sheath 9 can be regulated. As a result, it is possible to prevent the advanced position A1 of the distal end tip 5 from retracting and the indwelling position of the stent 100 from deviating from a desired position due to an operation of retracting the second sheath 8 performed to indwell the stent 100.

Next, when the indwelling position of the stent 100 is adjusted, recapturing operation can be performed. Specifically, in a state in which the position of the delivery device 1 is held with respect to the insertion portion 210 of the endoscope 200, the stent 100 is accommodated within the stent storage region E1 by advancing the second sheath 8 and advancing the distal end 81 of the second sheath 8 with respect to the first sheath 7 (Step S4). The surgeon P2 advances the operation portion 4 to the distal side L1 while holding the handle 3. Due to this operation, when the second sheath 8 is advanced, forces act on the third sheath 9 to the outward side of bending of the sheath main body 10, namely, in directions indicated by the arrows B81, B82, and B83 in FIG. 8. Since the position of the handle 3 is held, when a force acts on the third sheath 9 in the directions of the arrows B81, B82, and B83, the adjuster 6 extends in the longitudinal direction and the proximal end 92 of the third sheath 9 is advanced. As a result, the path length from the proximal end portion 32 of the handle 3 to the distal end 91 of the third sheath 9 is lengthened, and the path length of the first sheath 7 inside the sheath main body 10 is lengthened. While the stent 100 is accommodated within the stent storage region E1, the first sheath 7 slightly retracts with respect to the second sheath 8. In this state, when the surgeon P2 cancels the state of holding the handle 3 at a predetermined position, the adjuster 6 contracts to an original length. As a result, the path lengths of the first sheath 7 and the second sheath 8 inside the sheath main body 10 with respect to the third sheath 9 return to the original length, the first sheath 7 and the second sheath 8 is advanced through the distal opening 231, the stent 100 is stored in the stent storage region E1, and recapturing operation is thereby completed. When recapturing operation is completed, the stent returns to the state before being released.

For example, a spring having a spring force of 3 N or smaller is used as the adjuster 6. Since a spring having a spring force of 3 N or smaller is used as the adjuster 6, when recapturing operation is performed, the spring extends in accordance with movement of the third sheath 9 to the proximal side L2. As a result, at the time of recapturing operation of the stent 100, the path length can be adjusted due to a biasing force of the adjuster 6 and the first sheath 7 is smoothly retracted without having movement of the third sheath 9 to the proximal side L2 adjusted by the surgeon P2. When a spring having a spring force greater than 3 N is used as the adjuster 6, the spring is unlikely to extend, and an effect of a spring is not exhibited in the delivery device 1 for indwelling the stent 100 inside a human body cavity. Regarding an adjuster or the like, using a spring having a spring force of 3 N or smaller is not necessarily an essential constitution, and it can be set in accordance with a rigidity or the like of the stent. In addition, the spring is a tight-winding spring. In a tight-winding spring, wound wires constituting the spring are wound by being closely disposed in a state in which there is almost no clearance therebetween. This is because positional misalignment at the time of indwelling of the stent can be prevented when it is constituted of a tight-winding spring.

Next, the stent 100 is indwelled. After the surgeon P1 positionally sets the distal end tip 5 at the indwelling position of the stent 100, in a state in which the surgeon P1 holds the position of the delivery device 1 with respect to the insertion portion 210 of the endoscope 200, similar to Step S3 described above, the surgeon P2 retracts the operation portion 4 to the proximal side L2 while holding the handle 3 and causes the stent 100 to protrude from the second sheath 8 (Step S5). Specifically, when the operation portion 4 is retracted with respect to the handle 3, the second sheath 8 retracts with respect to the first sheath 7. As a result, the first sheath 7 protrudes from the distal end 81 of the second sheath 8 and increases in diameter. When a proximal end of the stent 100 is exposed on a distal side of a distal end of the second sheath 8, the stent 100 further increases in diameter than the distal end tip 5. As illustrated in FIG. 3, at the indwelling position, the stent 100 widens the stenosed site T1. The handle 3 is retracted, and the distal end tip 5 is retracted from the inward side of the stent 100 which has increased in diameter, thereby completing indwelling of the stent 100 (Step S5). After indwelling of the stent 100, the delivery device 1 is withdrawn from the channel 230 and indwelling of the stent 100 is completed. Steps S3 and S4 are repeated until the position of the distal end tip 5 can be disposed at a desired position. If the position of the distal end tip 5 can be disposed at a desired position when Step S3 is performed for the first time, there is no need to perform Step S4.

According to the delivery device 1, the delivery system 300, and the method for indwelling a stent of to the present embodiment, a treatment tool can be disposed accurately and smoothly at a treatment target part.

According to the method for indwelling a stent of the present embodiment, the stent 100 can be disposed accurately and smoothly at a stenosed site. According to the method for indwelling a stent of the present embodiment, recapturing operation of the stent 100 can be smoothly performed.

According to the delivery device 1 of the present embodiment, since the adjuster 6 is provided, the distance D1 between the proximal end 72 of the first sheath 7 and the distal end 91 of the third sheath 9 in the longitudinal direction L can be changed between the first distance and the second distance. As a result, misalignment of the indwelling position of the stent 100 at the time of advance-retract operation of the second sheath 8 due to relative positional misalignment of a distal end of the first sheath 7 is possible to be prevented.

According to the delivery device 1 of the present embodiment, the self-expanding stent 100 having engagement portions can be disposed within the stent storage region E1. Namely, during recapturing operation of the self-expanding stent 100, the first sheath 7 can be smoothly retracted with respect to the second sheath 8. As a result, in each of the wires 100*a*, 100*b*, and 100*c* which has exposed to the outside and expanded, the engagement portions are prevented from being broken and stuck with respect to the longitudinal direction L between the lumen and the lumen 83 of the second sheath 8.

According to the delivery device 1 of the present embodiment, since the adjuster 6 is provided between the proximal end 72 of the first sheath 7 and the distal end 91 of the third sheath 9, the distance between the proximal end 72 of the first sheath 7 and the distal end 91 of the third sheath 9 in the longitudinal direction L is easily adjusted. Specifically, since the adjuster 6 capable of changing the path length between the proximal end 72 of the first sheath 7 and a distal end of the third sheath 9 is provided, change in relative position of the third sheath 9 due to change in path length between the first sheath 7 and the second sheath 8 can be automatically adjusted using the adjuster 6. Therefore, even if the path length between the first sheath 7 and the second sheath 8 changes at the time of indwelling, treatment is smoothly performed.

According to the delivery device 1 of the present embodiment, the length of the third sheath 9 is shorter than the lengths of the first sheath 7 and the second sheath 8. As a result, even in a three-layer sheath structure, the third sheath 9 is disposed on the proximal side of the distal end portions of the first sheath 7 and the second sheath 8, motion of the first sheath 7 and the second sheath 8 at the time of indwelling of the stent 100 is smoothly performed. Further-more, the delivery device 1 can perform smooth advance-retract operation and bending operation of the sheath main body 10.

Figure 9:
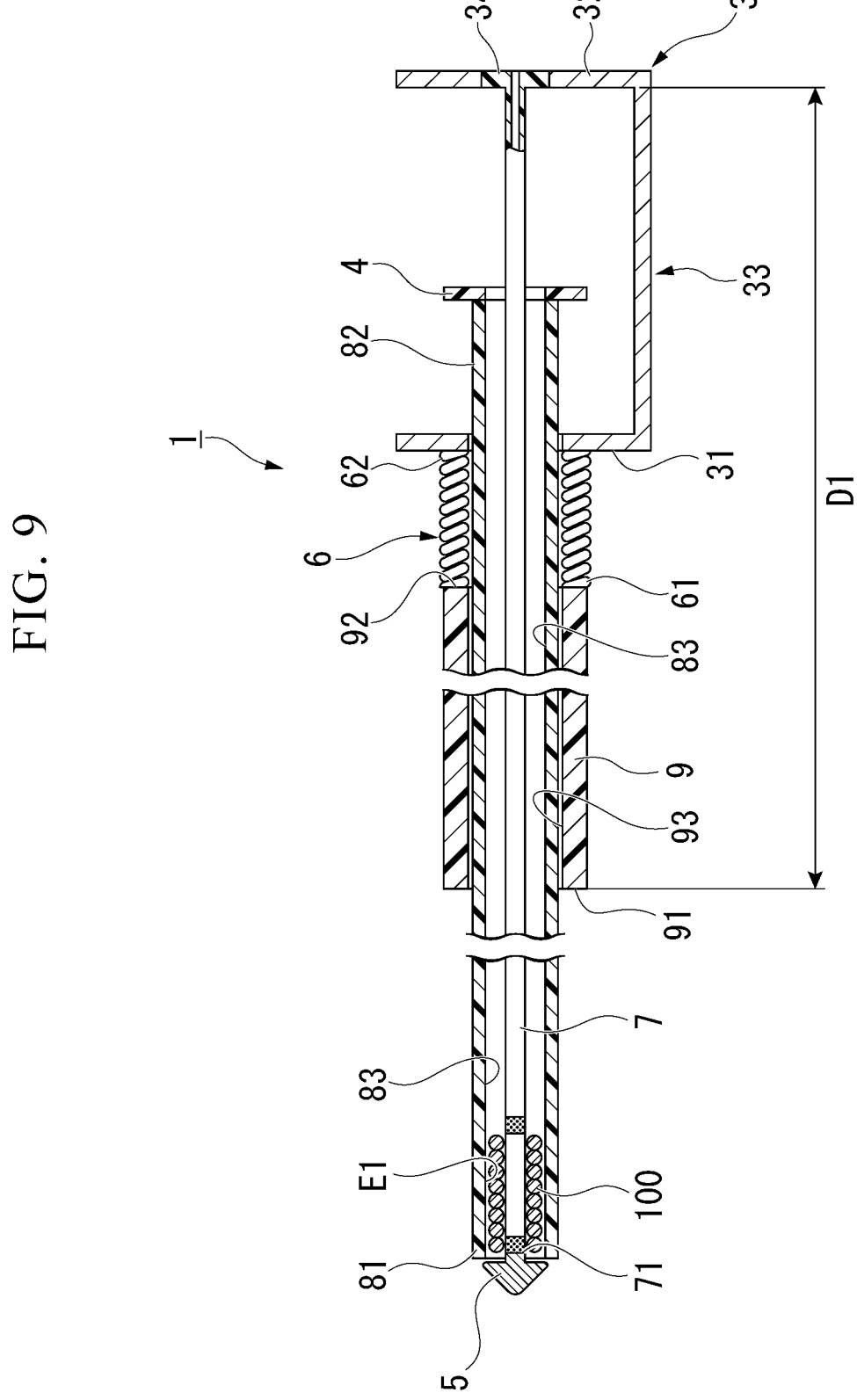
FIG. 9 is a cross-sectional view of the delivery device according to a modified example of the first embodiment.

In the present embodiment, an example in which the adjuster 6 is a tubular coil spring through which the second sheath 8 can be inserted has been described, but the shape of the adjuster 6 is not limited to a tubular shape. The adjuster 6 may only have a configuration that the distance between the proximal end 72 of the first sheath 7 and the distal end 91 of the third sheath 9 in the longitudinal direction L is capable of changing between the first distance and the second distance. For example, the adjuster may be a leaf spring, a bellows-like tube, an elastic member, other extensible-contractable members, or the like fixed to the distal end 91 of the third sheath 9 and the distal end portion 31 of the handle 3. For example, as illustrated in FIG. 9, a plurality of tight-winding coil springs may be used as the adjuster 6. The example illustrated in FIG. 9 is an example of the adjuster 6 in which a plurality of tight-winding coils are disposed away from each other in the circumferential direction of the third sheath 9. When a plurality of coil springs are used as an adjuster, characteristics such as an initial tensile force or an elastic modulus of the coils may be the same or may be different from each other.

Figure 10:
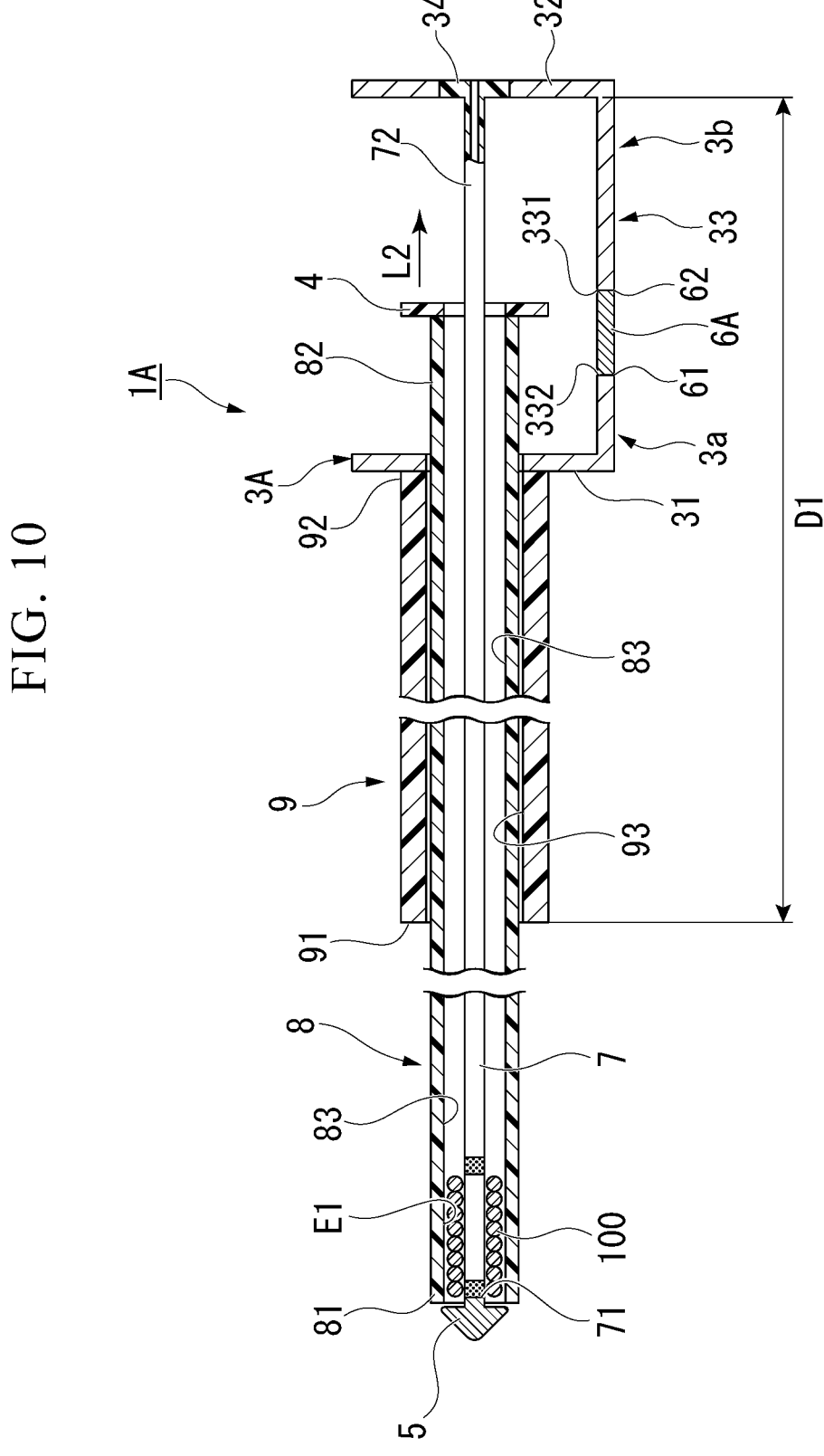
FIG. 10 is a cross-sectional view of a delivery device according to a second embodiment.

A delivery device 1A according to a second embodiment will be described with reference to FIG. 10. In the following description, the same reference signs are applied to common constitutions which have already been described, and duplicate description thereof will be omitted. FIG. 10 is a cross-sectional view of the delivery device 1A according to the present embodiment.

Second Embodiment

The delivery device 1A differs from that of the first embodiment in the shape of the handle and the constitution of the adjuster. The proximal end 92 of the third sheath 9 is fixed to the distal end portion 31 of a handle 3A. The handle 3A includes a first member 3a and a second member 3b which are provided side by side in the longitudinal direction L. A portion of the intermediate portion 33 of the handle 3A in the circumferential direction opens. The handle 3A may have a substantially U-shaped cross section. An adjuster 6A is provided between the proximal end 72 of the first sheath 7 and the distal end 91 of the third sheath 9. A distal end 61 of the adjuster 6A is fixed to a proximal end 332 of the first member 3a, and the proximal end 62 of the adjuster 6A is fixed to a distal end 331 of the second member 3b. The first member 3a may correspond to a first body member. The second member 3b may correspond to a second body member. Similar to the first embodiment, for example, the adjuster 6A is a leaf spring, an elastic member, a coil spring having a central axis disposed along the intermediate portion 33, or the like. The length adjustment mechanism may be between the first body member and the second body member and, when operated, the length adjustment mechanism adjusts to move the first body member and the second body member toward or away from each other.

Operations of the delivery device 1A, the delivery system, and the method for indwelling a stent using the delivery device 1A are similar to those of the first embodiment. That is, the adjuster 6 contracts during Step S3 in the method for indwelling a stent described above and holds a distance D1 at the first length. During D Step S4, when a force caused by bending or meandering of the second sheath 8 inside the lumen 93 of the third sheath 9 acts on the third sheath 9 or when the path length of the first sheath 7 is lengthened, the adjuster 6A extends and the first member 3a moves to the distal side L1 with respect to the second member 3b so that the distance D1 can be changed to the second length.

According to the delivery device 1A of the present embodiment, similar to the first embodiment, a treatment tool can be disposed accurately and smoothly at a treatment target part.

According to the delivery device 1A of the present embodiment, since the adjuster 6A is provided, the distance D1 between the proximal end 72 of the first sheath 7 and the distal end 91 of the third sheath 9 in the longitudinal direction L can be changed between the first distance and the second distance. As a result, misalignment of the indwelling position of the stent 100 at the time of advance-retract operation of the second sheath 8 due to relative positional misalignment of a distal end of the first sheath 7 is possible to be prevented.

According to the method for indwelling a stent of the present embodiment, the stent 100 can be disposed accurately and smoothly at a stenosed site. According to the method for indwelling a stent of the present embodiment, recapturing operation of the stent 100 is smoothly performed.

The shape of the handle is not limited to the example illustrated in FIG. 10 and it may need only be a connected handle with the adjuster 6A therebetween in the longitudinal direction L. Similar to the first embodiment, a handle having a rectangular hollow cross-sectional shape may be constituted in a separate manner in an intermediate part in the longitudinal direction L, and an adjuster may be provided in the intermediate portion 33.

Third Embodiment

Figure 11:
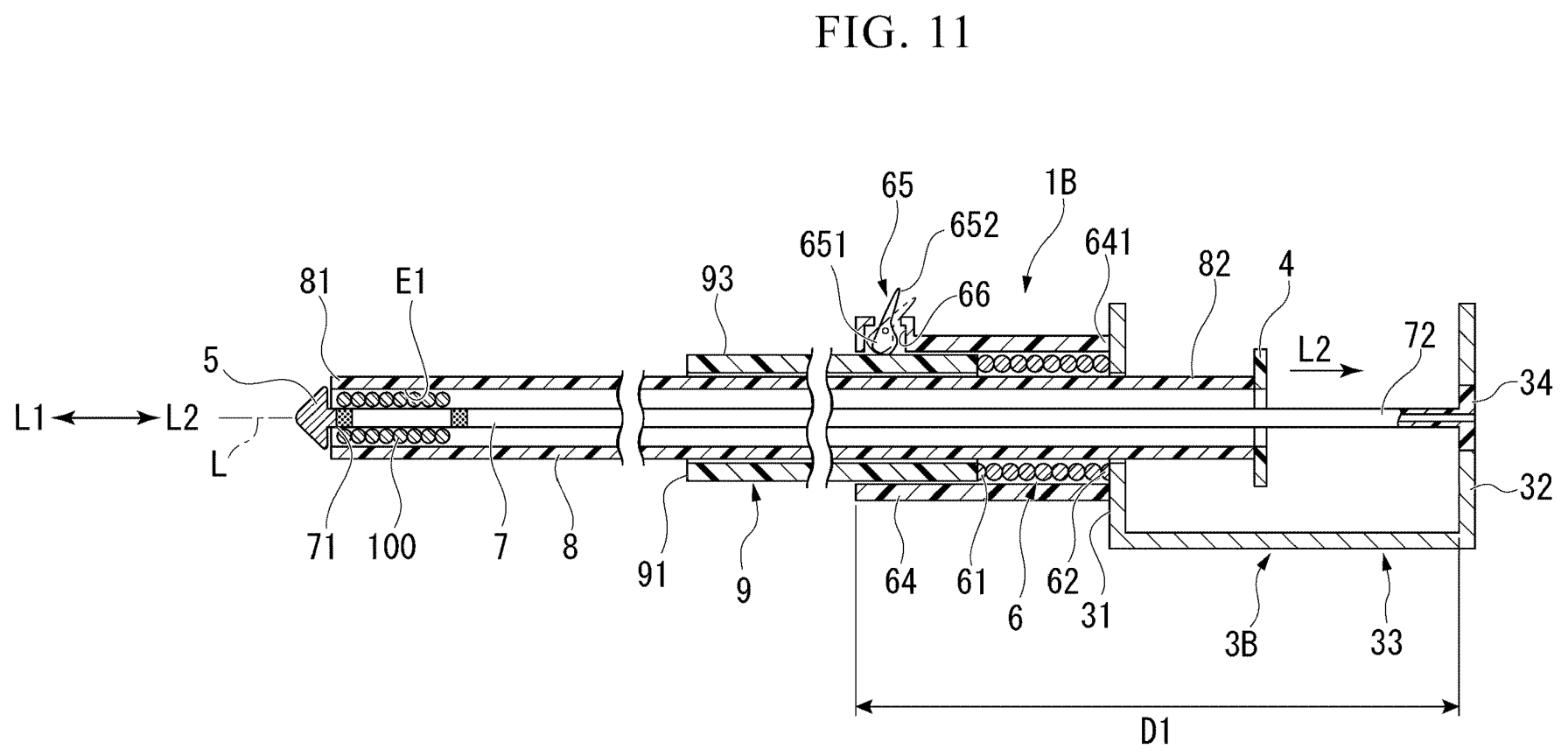

A delivery device 1B according to a third embodiment will be described with reference to FIG. 11. In the following description, the same reference signs are applied to common constitutions which have already been described, and duplicate description thereof will be omitted. The delivery device 1B according to the present embodiment differs from that of the first embodiment in that a protective sheath 64 and the lock mechanism 65 are provided. The constitution of the adjuster 6 is similar to that of the first embodiment. A portion of the intermediate portion 33 of a handle 3B in the circumferential direction opens. The handle 3A may have a substantially U-shaped cross section. For example, the distal end portion 31 may be provided at a distal end of the plate-shaped intermediate portion 33, and the proximal end portion 32 may be disposed such that if faces the proximal end in a separated manner.

For example, the protective sheath 64 is a resin sheath. A proximal end 641 of the protective sheath 64 comes into contact with the distal end portion 31 of the handle 3. The protective sheath 64 covers the proximal end 92 of the third sheath 9 and the adjuster 6. The protective sheath 64 is separated from the adjuster 6 in the circumferential direction so as not to hinder extension and contraction of the adjuster 6.

The lock mechanism 65 is provided in a distal portion of the protective sheath 64. Specifically, an accommodation portion 66 communicating with the inside and the outside of the protective sheath 64 is formed, and a lock main body 651 is accommodated inside the accommodation portion 66. A switching portion 652 is provided such that it is integrally formed with the lock main body 651 and protrudes to the outward side in a diameter direction from the accommodation portion 66. The lock main body 651 has a lock surface which can tightly adhere to an outer surface of the third sheath 9, and a non-lock surface which is disposed so as to be separated from an outer circumferential surface of the third sheath 9. In response to a moving operation of the switching portion 652, the lock main body 651 turns inside the accommodation portion 66, and the lock surface or the non-lock surface faces the outer surface of the third sheath 9. When the switching portion 652 is disposed at a first position, the lock surface tightly adheres to the outer surface of the third sheath 9, and thus relative positions of the third sheath 9 and the protective sheath 64 are fixed. When the switching portion 652 is disposed at a second position different from the first position, the lock main body 651 turns, and the non-lock surface faces the outer surface of the third sheath 9 at a position away therefrom. In this state, the third sheath 9 is capable of advancing and retracting with respect to the protective sheath 64.

Operations of the delivery device 1B, the delivery system, and the method for indwelling a stent using the delivery device 1B are similar to those of the first embodiment. That is, the adjuster 6 contracts during Step S3 in the method for indwelling a stent described above and holds the distance D1 at the first length. During Step S4, when a force caused by bending or meandering of the second sheath 8 inside the lumen 93 of the third sheath 9 acts on the third sheath 9 or when the path length of the first sheath 7 is lengthened, the adjuster 6A extends and the first member 3a moves to the distal side L1 with respect to the second member 3b so that the distance D1 can be changed to the second length.

In the delivery device 1B, when it is intended to perform operation while the position of the handle 3B with respect to the third sheath 9 is fixed, such as when the distal ends of the first sheath 7 and the second sheath 8 is positionally set, the relative positions of the protective sheath 64 and the third sheath 9 can be held due to the lock mechanism 65 by operating the switching portion 652 to be at the first position. When recapturing operation of the stent 100 is performed or the like using the delivery device 1B, the adjuster 6 and the proximal end 92 side of the third sheath 9 is possible to advance and retract by disposing the switching portion 652 at the second position and unlocking the lock mechanism 65.

According to the delivery device 1B of the present embodiment, similar to the first embodiment, a treatment tool is disposed accurately and smoothly at a treatment target part.

According to the delivery device 1B of the present embodiment, since the adjuster 6 is provided, the distance D1 between the proximal end 72 of the first sheath 7 and the distal end 91 of the third sheath 9 in the longitudinal direction L can be changed between the first distance and the second distance. As a result, it is possible to prevent and misalignment of the indwelling position of the stent 100 at the time of advance-retract operation of the second sheath 8 due to relative positional misalignment of a distal end of the first sheath 7 is possible to be prevented.

The constitution of the lock mechanism 65 is not limited to the example described above. The lock mechanism may only have a constitution in which a position of the protective sheath 64 can be fixed and unfixed with respect to the third sheath 9. For example, it may have a constitution in which a portion of an inner wall of the protective sheath 64 decreases in diameter and is tightly adhered and fixed to the outer surface of the third sheath 9 in response to an operation of the switching portion, and a portion of the inner wall of the protective sheath 64 increases in diameter, is separated from the outer surface of the third sheath 9, and is unfixed in response to an operation of the switching portion. That is, a lock mechanism 65 is configured to reversibly fix a position of the protective sheath 64 relative to the third sheath 9.

In the delivery device 1 according to the foregoing embodiment, an example in which a protective sheath includes a lock mechanism has been described, but the lock mechanism is not an essential constitution in regard to the purpose of covering the adjuster 6.

In each of the foregoing embodiments, an example in which the stent 100 is a self-expanding stent has been described, but in regard to the purpose of accurately indwelling a stent at a desired position using a delivery device, the stent 100 is not limited to a self-expanding stent. The stent 100 may be a non-self-expanding stent. Examples thereof include stents made of a CoCr-based alloy and biodegradable stents made of polylactic acid, polyglycolic acid, or a copolymer thereof. The stent 100 may be a stent expanding by means of a fluid. Examples of stents expanding by means of a fluid include a non-self-expanding stent expanding by means of other treatment tools such as a balloon.

In the foregoing embodiments, an example of the delivery device 1 in which the stent 100 is indwelled has been described, but examples of use of the delivery device is not limited to indwelling of the stent 100. For example, the delivery device can be applied to examples having a treatment tool such as a guide wire or forceps to be inserted through the first sheath so as to be capable of advancing and retracting, or the delivery device 1 in which a liquid feeding lumen is provided in the first sheath and which is used for liquid feeding.

Hereinabove, embodiments have been described in detail with reference to the drawings, but the specific constituents are not limited to the embodiments, and the present disclosure also includes design change and the like within a range not departing from the gist of the present disclosure. In addition, the constituent elements illustrated in the embodiments and the modified examples described above can be suitably constituted in combination.

What is claimed is:

1. A delivery device, comprising:
   a handle;
   a first sheath having a proximal end portion connected to the handle;
   a second sheath through which the first sheath is inserted, the second sheath translatable relative to the handle in a longitudinal direction of the delivery device;
   a third sheath through which the second sheath is inserted;
   a length adjustment mechanism;
   a protective sheath covering the third sheath and the length adjustment mechanism; and
   a lock mechanism configured to reversibly fix a position of the protective sheath relative to the third sheath,
   wherein a distance in the longitudinal direction of the delivery device between a proximal end of the first sheath and a distal end of the third sheath defines a separation distance,
   wherein the length adjustment mechanism adjusts the separation distance between a first length and a second length,
   wherein the second length is longer than the first length,
   wherein a distal end of the length adjustment mechanism is fixed to a proximal end of the third sheath, and a proximal end of the length adjustment mechanism is fixed to the handle, and

wherein the protective sheath covers the proximal end of the third sheath, and a proximal end of the protective sheath comes into contact with a distal end portion of the handle.

2. The delivery device according to claim 1, wherein the length adjustment mechanism includes a biasing member, and wherein the biasing member variably biases the third sheath relative to the first sheath in the longitudinal direction of the delivery device.

3. The delivery device according to claim 1, wherein the length adjustment mechanism is located between the proximal end of the first sheath and the distal end of the third sheath.

4. The delivery device according to claim 1, wherein the first sheath has a first length, the second sheath has a second length, and the third sheath has a third length, and wherein the third length is less than the first length and the third length is less than the second length.

5. The delivery device according to claim 1, wherein the first sheath, the second sheath, and the third sheath are configured to be insertable into a channel of an endoscope.

6. The delivery device according to claim 1, further comprising:

a stent disposed between an outer circumferential surface of the first sheath and an inner surface of the second sheath, wherein, in the longitudinal direction of the of the delivery device, the stent is positioned more distal than the distal end of the third sheath.

7. The delivery device according to claim 6, wherein the stent includes a plurality of wires, and wherein each of the plurality of wires includes:

a first plurality of first bent portions in which the wire is bent in a first direction, and a second plurality of second bent portions in which the wire is bent in a second direction, the second direction opposite to the first direction, and a plurality of engagement portions in which first bent portions of a first wire of the plurality of wires intersects second bent portions of a second wire of the plurality of wires.

8. The delivery device according to claim 1, wherein the length adjustment mechanism includes a spring having a spring force of 3 N or smaller.

*     *     *     *     *